(12) United States Patent
Cloutier et al.

(10) Patent No.: US 8,132,444 B2
(45) Date of Patent: Mar. 13, 2012

(54) PROTECTIVE HEATED SCREEN FOR ELEMENT

(75) Inventors: Paul Cloutier, White Lake, MI (US); Zhe Huang, Farmington Hills, MI (US)

(73) Assignee: DENSO International America, Inc., Southfield, MI (US)

( * ) Notice: Subject to any disclaimer, the term of this patent is extended or adjusted under 35 U.S.C. 154(b) by 486 days.

(21) Appl. No.: 12/415,468

(22) Filed: Mar. 31, 2009

(65) Prior Publication Data

US 2010/0242574 A1    Sep. 30, 2010

(51) Int. Cl.
*G01N 7/00* (2006.01)
(52) U.S. Cl. ..................... 73/31.05; 73/23.31
(58) Field of Classification Search ........... 73/31.05, 73/23.31, 23.32, 23.33
See application file for complete search history.

(56) References Cited

U.S. PATENT DOCUMENTS

| | | | | |
|---|---|---|---|---|
| 4,199,424 A * | 4/1980 | Teitelbaum | | 204/428 |
| 6,242,263 B1 * | 6/2001 | Faber et al. | | 436/143 |
| 6,658,916 B2 * | 12/2003 | Donelon et al. | | 73/23.31 |
| 7,493,796 B2 * | 2/2009 | Wilde | | 73/23.31 |
| 8,001,827 B2 * | 8/2011 | Weyl et al. | | 73/23.31 |
| 2008/0105030 A1 * | 5/2008 | Wilde | | 73/23.31 |

* cited by examiner

*Primary Examiner* — Lisa Caputo
*Assistant Examiner* — Punam Roy
(74) *Attorney, Agent, or Firm* — Harness, Dickey & Pierce, PLC

(57) ABSTRACT

A protective heated screen for an element of a sensor surrounds a portion of the element and reduces and/or minimizes the propensity for liquid droplets to come in contact with the heated element. The screen can allow fluid flow therethrough to allow the sensor element to come in contact with the fluid stream. The screen can be in continuous heat-transferring contact with the sensor element such that both the sensor element and screen are at a temperature significantly greater than the ambient temperature. Liquid droplets contacting the heated screen may evaporate such that the liquid droplets do not come in contact with the sensor element. The screen can also break down the liquid droplets into smaller droplets such that the thermal stress created by the droplets contacting the heated element is reduced over that caused by a larger droplet.

19 Claims, 3 Drawing Sheets

PROTECTIVE HEATED SCREEN FOR ELEMENT

FIELD

The present disclosure relates to protection for sensor elements and, more particularly, to protective heated screens for elements of a gas sensor.

BACKGROUND AND SUMMARY

This section provides background information related to the present disclosure which is not necessarily prior art. This section also provides a general summary of the disclosure, and is not a comprehensive disclosure of its full scope or all of its features.

Sensors, such as gas sensors used in automotive vehicle systems, can include elements that are susceptible to excessive thermal stress that can result in failure of the sensor. These sensor elements can be heated and, as a result, if the heated element comes in contact with a fluid of a lower temperature, thermal stress can be created in the element. The thermal stress may lead to degradation in performance or failure. By way of non-limiting example, such gas sensors can include oxygen sensors, air/fuel sensors, and NOx sensors used in the exhaust systems of automotive vehicles. These gas sensors include elements that are heated to an operating temperature to perform their intended function. The heated sensor elements are exposed to the exhaust gases flowing through the exhaust system. Water vapor in the exhaust streams may condense in the exhaust system and/or on the sensor during some operating conditions. One such operating condition can include operation under winter conditions. Due to the elevated temperature of the sensor element, if the water droplets were to come in contact with the element, thermal stress can occur. Excessive thermal stress can lead to damage to the element and degradation in performance or failure of the sensor. Accordingly, it is advantageous to minimize the possibility of water droplets in the exhaust system from contacting the sensor element to reduce the potential for thermal stress.

A protective heated screen for an element of a sensor, according to the present teachings, surrounds a portion of the element and reduces and/or minimizes the propensity for water droplets to come in contact with the heated element. The screen can allow fluid flow therethrough to allow the sensor element to come in contact with the fluid stream, thereby allowing the sensor to perform its intended function. The screen can be in continuous heat-transferring contact with the sensor element such that both the sensor element and screen are at a temperature significantly greater than the ambient temperature. The screen can be a mesh that allows gaseous fluid to flow therethrough. Water droplets contacting the heated screen may evaporate such that the liquid water droplets do not come in contact with the sensor element. The screen can also break down the water droplets into smaller droplets such that the thermal stress created by the water droplets contacting the heated element is reduced over that caused by a larger water droplet.

A gas sensor according to the present teachings includes a gas-sensing element operative to detect a concentration of a specified gas in a gas flow. A heating element is operative to heat the gas-sensing element to an operating temperature. A housing supports the gas-sensing element. A screen with a plurality of ventilation openings is disposed exterior to the gas-sensing element. The screen surrounds the leading end portion of the gas-sensing element such that a gas flow travels through the ventilation openings prior to reaching the gas-sensing element. A first portion of the screen is in continuous direct heat-transferring contact with the gas-sensing element such that heat generated by the heating element is transferred to the screen through the gas-sensing element. A second portion of the screen is spaced apart from the gas-sensing element with a first gap therebetween.

A method of operating a gas sensor to detect a concentration of a specified gas in a gas flow while reducing a possibility of liquid droplets contacting the gas-sensing element according to the present teachings includes surrounding a leading end portion of the gas-sensing element with a screen having a plurality of ventilation openings and disposed exterior to the gas-sensing element such that the gas flow travels through the ventilation openings prior to reaching the gas-sensing element. The screen having a first portion in continuous direct heat-transferring contact with the gas-sensing element and a second portion spaced apart from the gas-sensing element with a first gap therebetween. The method includes heating the gas-sensing element to an operating temperature with a heating element and heating the screen to an operating temperature with heat transfer from the gas-sensing element to the first portion of the screen. The method includes evaporating liquid droplets in the gas flow that contact the screen and detecting the concentration of the specified gas in the gas flow.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 4 is an enlarged view of a portion of the protective heated screen according to the present teachings;

Corresponding reference numerals indicate corresponding parts throughout the several views of the drawings.

DETAILED DESCRIPTION

Example embodiments will now be described more fully with reference to the accompanying drawings.

In the following description, it is construed that a portion of the sensor adapted to be inserted into an exhaust pipe of an internal combustion engine of a motor vehicle is referred to as a "leading end" or a "leading end portion" and an opposite side of the gas sensor exposed to an atmosphere is referred to as a "base end" or a "base end portion."

Further, it should be appreciated that the protective heated screen according to the present teachings may have a wide variety of applications in a variety of sensors, such as an oxygen sensor, an air/fuel sensor, and a NOx sensor, by way of non-limiting example.

Figure 1:
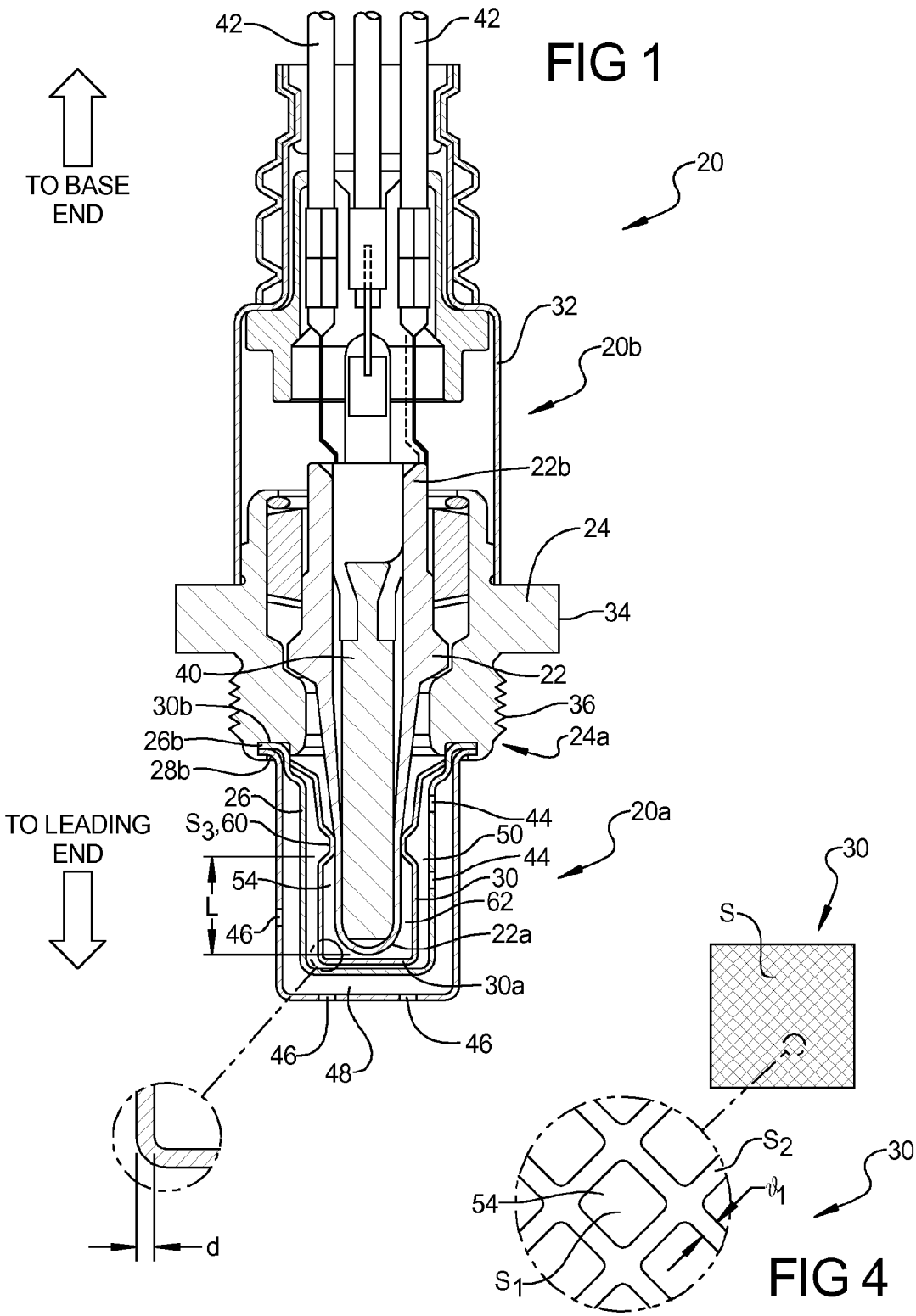
FIG. 1 is a longitudinal cross-sectional view showing an overall structure of a gas sensor utilizing a protective heated screen for the element according to the present teachings.

Referring to FIG. 1, a longitudinal cross-sectional view showing an overall structure of a gas sensor 20 according to the present teachings is shown. Gas sensor 20 includes a gas-sensing element 22 for detecting a concentration of a specified gas in a gas stream. A housing 24 internally holds element 22. Inner and outer covers 26, 28 and a heated protective screen 30 are fixedly secured to housing 24 at a leading end thereof so as to cover a leading end 22a of element 22. An atmospheric cover 32 is fixedly secured to housing 24 at a base end thereof so as to cover a base end 22b of element 22.

Housing 24 can include a plurality of flat surfaces 34 and threads 36 that facilitate the mounting of gas sensor 20 on a wall surface of an exhaust pipe (not shown) extending from an automotive vehicle engine. The flat surfaces 34 allow gas sensor 20 to be rotated by means of a wrench or other device while threads 36 engage with complementary threads in the wall of the exhaust pipe. When installed, the leading end portion 20a communicates with the exhaust gas stream flowing through the exhaust pipe while the base end portion 20b communicates with the atmosphere exterior to the exhaust pipe.

Leading end 22a of element 22 communicates with the exhaust gases flowing through the exhaust pipe while base end 22b communicates with the atmosphere exterior to the exhaust pipe. Element 22 is operable to measure properties of a particular gas in the exhaust gas stream within the exhaust pipe and provide a signal indicative of the measured gas that may be used to control the operation of the automotive engine and/or vehicle. By way of non-limiting example, gas sensor 20 can create an ion flow across element 22 wherein a difference in partial pressure between leading end 22a and base end 22b (a reference end) creates electrical potential that varies as a function of a particular gas in the exhaust gas flow.

To facilitate the detection of the gas in the exhaust gas flow, element 22 is heated. A resistive load 40 is disposed within the leading end portion 22a of element 22. The resistive load 40 forms a heater that is powered by electrical current provided by power wires 42. The resistive load 40 can be alumina with platinum electrodes. The resistive load 40 can be concentrated in the leading end 22a of element 22. For example, the resistive load 40 can be located in element 22 such that the resistive load 40 only extends from about 5 mm to about 10 mm from leading end 22a. Resistive load 40 can provide a rapid temperature increase of element 22 to bring it up to operating conditions. By way of non-limiting example, resistive load 40 can warm element 22 up to operating conditions within 10 seconds or less. Additionally, resistive load 40 can provide heat element 22 up to an operating temperature in the range of about 600° C. to about 1000° C., by way of non-limiting example. The elevated temperature facilitates performance of element 22 along with helping to prevent poisoning of element 22 such as by silicon, carbon, sulfur, or other contaminants that may be contained within the exhaust gas stream. As a result, element 22 operates at a temperature significantly greater than the atmospheric temperature exterior to the exhaust pipe. Element 22 can be a ceramic, such as yttria stabilized zirconia by way of non-limiting example, and can have and exterior catalyzing layer, including alumina by way of non-limiting example.

To allow the exhaust gas stream within the exhaust pipe to contact element 22, inner and outer covers 26, 28 each include a plurality of respective openings 44, 46. Openings 44 in inner cover 26 are offset from openings 46 and outer cover 28 such that the exhaust gas flow in the exhaust pipe does not flow directly through both openings 46 in outer cover 28 and openings 44 in inner cover 26. Rather, the exhaust gas flow changes direction within a gap 48 between inner and outer covers 26, 28. The number and location of openings 44, 46, along with their size, are selected in order to provide the desired quantity of exhaust gas flow through gas sensor 20. The staggering (offsetting) of openings 44, 46 helps inhibit the occurrence of water droplets within the exhaust gas stream from contacting element 22 which can cause thermal stress due to the elevated temperature of element 22. Inner and outer covers 26, 28 can be rigid covers and can be made from a variety of materials. For example, inner and outer covers 26, 28 can be inconel, stainless steel, and the like, by way of non-limiting example. It should be appreciated that the larger the size of openings 44, 46 the greater the amount of exhaust gas flowing through gas sensor 20 which may result in an improvement in the response time of gas sensor 20. However, as the size of openings 44, 46 increases, the chance of water droplets entering the interior of gas sensor 20 and contacting element 22 also increases. Thus, a balance is required between the number, size, and location of openings 44, 46 relative to the desired response time and the desired level of protection against water droplets entering into gas sensor 20. In a non-limiting example, openings 44, 46 can be about 2 mm to about 3 mm in diameter.

Gas sensor 20, according to the present teachings, utilizes a heated protective screen 30 to provide additional protection for element 22 against thermal stresses associated with the possibility of water droplets contacting element 22. Screen 30 surrounds the leading end portion 22a of element 22. Screen 30 is secured to housing 24 along with inner and outer covers 26, 28. Specifically, screen 30, inner cover 26, and outer cover 28 can have base ends 30b, 26b, and 28b that may be in the form of annular flanges that can be secured to leading end 24a of housing 24, such as by crimping, welding, and the like, by way of non-limiting example. Screen 30 is configured to have a gap 50 between screen 30 and inner cover 26. In this manner, the physical contact between screen 30 and inner cover 26 can be limited to the contact at the base end flanges.

Screen 30, as best seen in FIG. 4, is a mesh with a plurality of openings 54 therein. Screen 30 can be a solid mesh, as shown, or can be woven by way of non-limiting example. Openings 54 allow the exhaust gas flow to travel around element 22, as discussed in more detail below.

A portion 60 of screen 30 is in continuous direct contact with element 22 such that screen 30 and element 22 are in continuous heat-transferring relation with one another. The contact portion 60 allows heat generated by resistive load 40 within element 22 to be transferred from element 22 to screen 30. As a result, the temperature of screen 30 is also elevated above that of the atmosphere exterior to the exhaust pipe when element 22 is heated by resistive load 40. The surface area of contact portion 60 of screen 30 in direct contact with element 22 can affect the quantity of heat transferred from element 22 to screen 30, as described below. Screen 30 can be flexible such that the continuous direct contact between screen 30 and element 22 does not cause the coating on element 22 to be rubbed off due to relative movement between the contact portion 60 and element 22 during assembly or operation of the engine and/or vehicle, which can induce vibrations. Screen 30 can be made from a variety of materials. For example, screen 30 can be made from stainless steel, inconel, and the like, by way of non-limiting example. To facilitate the heat transfer and the elevating of the temperature of screen 30, screen 30 can be made from a material that is a good conductor of heat.

Figure 2:
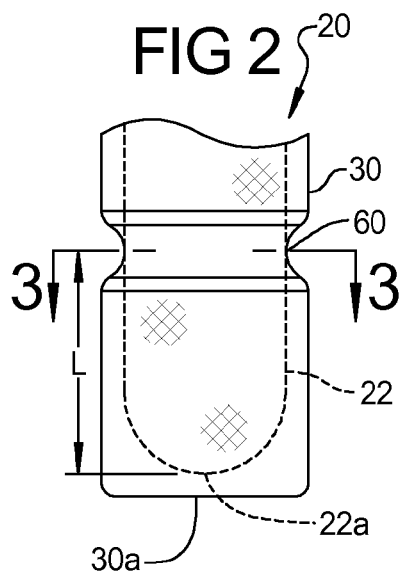
FIG. 2 is a fragmented plan view of the sensor element and the protective heated screen of FIG. 1.
Figure 3:
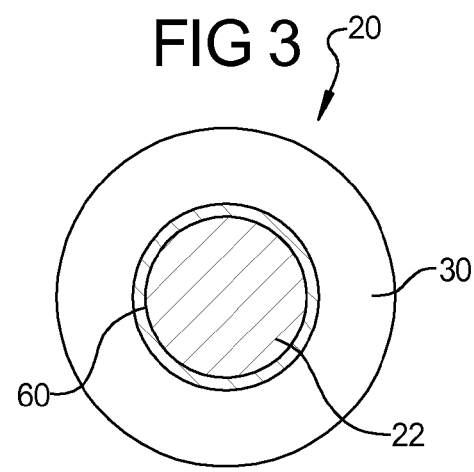
FIG. 3 is an enlarged cross-sectional view along lines 3-3 of FIG. 2.

The contact between screen 30 and element 22 can take a variety of configurations. For example, as shown in FIGS. 1-3, contact portion 60 can be a continuous contact band that circumscribes element 22. When the exterior of element 22 is cylindrical, then the continuous contact band is an annular band, as shown. The contact portion 60 can be located a distance L from the leading end 22a of element 22, where a majority of the heat is generated. The contact portion 60 can have a smaller diameter then the rest of screen 30. The remaining portion of screen 30 can have a larger diameter and be spaced apart from element 22 such that a gap 62 exists between screen 30 and element 22. To reduce the possibility of water droplets contacting screen 30 at the location of contact portion 60, contact portion 60 can be staggered from the location of openings 44 in inner cover 26. Gap 62 allows for water droplets to contact screen 30 without simultaneously contacting element 22.

Figure 5:
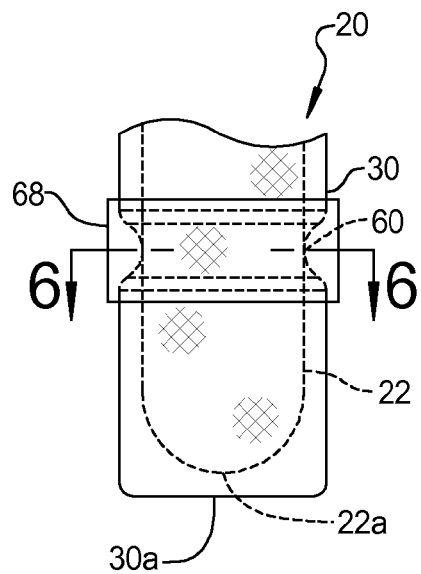
FIG. 5 is a fragmented plan view of the sensor element and an alternate configuration for the protective heated screen according to the present teachings.
Figure 6:
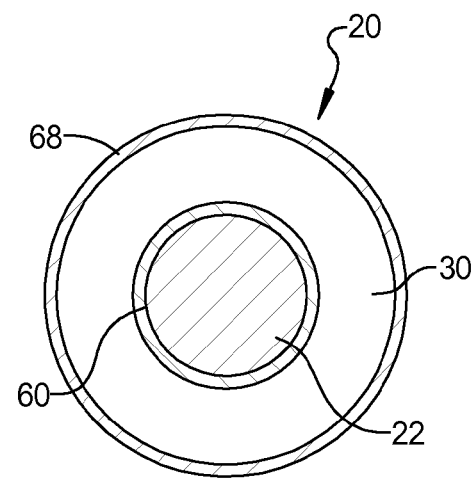
FIG. 6 is an enlarged cross-sectional view along lines 6-6 of FIG. 5.

To provide additional protection against the possibility of water droplets within gap 50 from contacting screen 30 at contact portion 60, a protective band 68, as shown in FIGS. 5 and 6, can circumscribe contact portion 60. Band 68 can be of the same construction as screen 30 and be in continuous direct heat-transferring contact with screen 30 such that band 68 may be at the same temperature as screen 30. Band 68 can be solid or include openings 54 such as those included in screen 30. The use of band 68 will cause water droplets within gap 50 to contact band 68 instead of contact portion 60. As a result, a protective heated screen can surround the leading end portion of element 22.

Figure 7:
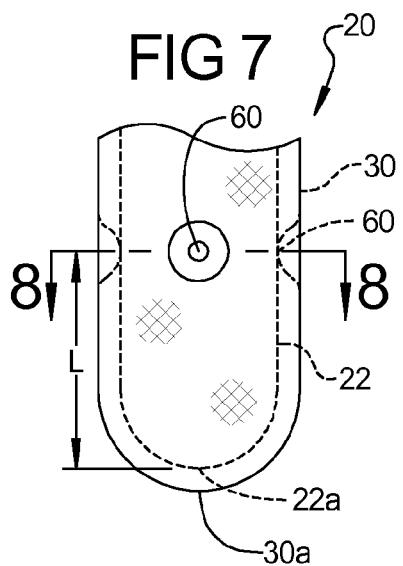
FIG. 7 is a fragmented plan view of the sensor element with another alternate configuration of a protective heated screen according to the present teachings.
Figure 8:
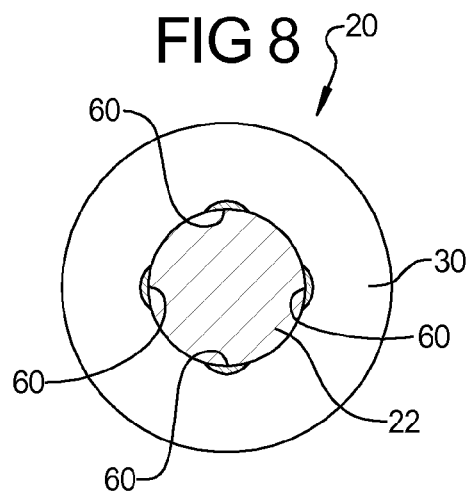
FIG. 8 is an enlarged cross-sectional view along lines 8-8 of FIG. 7.

In some configurations, such as that shown in FIGS. 7 and 8, the contact portion 60 can be one or more discrete points of continuous direct contact. In the configuration of FIGS. 7 and 8, there are four discrete contact portions 60 wherein screen 30 is in continuous direct heat-transferring contact with element 22. The contact portion 60 can be formed with depressions formed in the exterior surface of screen 30 such that discrete portions of screen 30 reach all the way in and provide continuous direct contact with element 22. It should be appreciated that the number and size of the discrete contact portions 60 can be varied from that shown and, furthermore, can be selected based on the criteria discussed below relative to the heat transfer between element 22 and screen 30. Additionally, it should be appreciated that while the discrete contact portions 60 are shown as being all at the same length L from leading end 22a of element 22, the various discrete contact portions 60 can be staggered such that they are at differing lengths from the leading end 22a.

Figure 9:
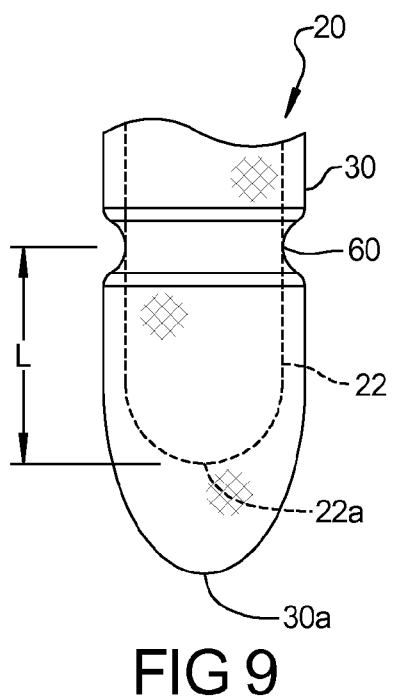
FIG. 9 is a fragmented plan view of the sensor element and still another configuration of a protective heated screen according to the present teachings.

The shape of screen 30 can vary as dictated by the exterior shape of element 22 and the interior shape of inner cover 26 so that gaps 62 and 50 are achieved. In some configurations, such as that shown in FIGS. 1, 2 and 5, the leading end 30a of screen 30 can be flat or planar. In other configurations, such as that shown in FIG. 7, leading end 30a can be rounded. In yet another configuration, as shown in FIG. 9, the leading end 30a can be conical.

Because screen 30 is heated by the continuous direct heat-transferring contact with element 22, screen 30 is at elevated temperature over that of the atmosphere exterior to the exhaust pipe. The temperature of screen 30 can be close to or the same as that of element 22. Due to the high temperature of element 22, screen 30 can also be at the high temperature such as between about 600° C. to about 1000° C., by way of non-limiting example. This high temperature can result in water droplets contacting screen 30 evaporating into the gaseous phase instead of penetrating therethrough and contacting element 22. Some water droplets contacting screen 30 may break down into smaller sized water droplets that fit within the openings 54 in screen 30 and contact element 22. However, these droplets are smaller than that which would be realized in the absence of screen 30. As a result, any water droplets passing through screen 30 will have a lower thermal stress impact on element 22 than would otherwise occur in the absence of screen 30. Therefore, screen 30 can reduce the size of water droplets contacting element 30 and/or cause the water droplets to evaporate to gaseous form before contacting element 22. Thus, screen 30 can advantageously reduce the propensity of water droplets that find their way into the interior of inner cover 26 from contacting element 22. The elevated temperature of screen 30 can prevent poisoning (or burn off) of screen 30, such as by silicon, carbon, sulfur, or other contaminates that may be contained in the exhaust gas stream.

Figure 10:
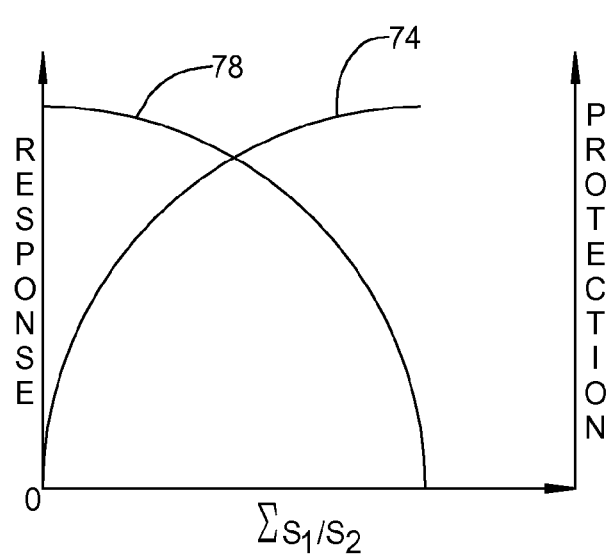
FIG. 10 is a hypothetical graph of the response of the sensor and the level of protection provided by the protective heated screen relative to the ratio of the area of the ventilation holes to the total area of the screen.

Various factors and design considerations can affect the configuration of screen 30 and that of gas sensor 20. One consideration is the balancing of the desire for protection from water droplets contacting element 22 thereby inducing thermal stresses versus the desire to have a sufficient exhaust gas flow across element 22 to ensure adequate performance of gas sensor 20. As shown in FIG. 4, $S_1$ can represent the area of a single ventilation opening 54 in screen 30. The area $S_1$ of each ventilation hole can be sized to be small enough to break down water droplets into a small enough size which will not cause excessive thermal stress on element 22 if the water droplet were to travel through the hole 54 and contact element 22. The total area of a solid portion of screen 30 can be represented by $S_2$. As a result, the total area S of screen 30 is the sum of all the areas $S_1$ ($\Sigma S_1$) of openings 54 and the area $S_2$. Referring now to FIG. 10, a hypothetical graph of the response of gas sensor 20 as a function of the ratio of the $\Sigma S_1/S_2$ is represented by curve 74. As can be seen, the response is zero when there are no openings 54 as no exhaust gas flow can flow across element 22. However, as the ratio increases, the response of gas sensor 20 increases. The graph of FIG. 10 also shows the hypothetical relationship between the protection provided by screen 30 as a function of the ratio as represented by curve 78. As can be seen, the protection provided is at the maximum when the ratio is zero (no openings 54). As the ratio increases, the level of protection provided by screen 30 decreases. Thus, one design consideration is to optimize the ratio of $\Sigma S_1/S_2$ to ensure that an adequate exhaust gas flow can travel through screen 30 and around element 22 while also ensuring that the desired level of protection against water droplets contacting element 22 is achieved.

Another design consideration is the quantity of energy consumed by heating screen 30. The energy consumption of screen 30 is related to the total volume/mass of screen 30. The thickness d, as shown in FIG. 1, of screen 30 and the total area S of the protective screen and the total area of actual material $S_2$ all affect the total volume/mass of screen 30. The thickness d and areas S and $S_2$ can be optimized to ensure the least amount of power consumption of screen 30 while still achieving a desired level of protection and response. Generally, the larger the thermal mass of screen 30, the more power that will be consumed to maintain screen 30 at a particular temperature.

Another design consideration is the area of contact $S_3$ between screen 30 and element 22. As stated above, the contact portion 60 can vary and, therefore, the contact area $S_3$ can also vary. The contact area $S_3$ can be optimized to maintain the temperature of screen 30 at a particular temperature. Generally, the larger the contact area $S_3$, the higher the temperature screen 30 will have for a given operating temperature of element 22. However, the increased contact area $S_3$ can result in a greater power consumption as the temperature of screen 30 will be higher than that of a reduced contact area $S_3$.

Another design consideration is the distance L between the contact portion 60 and the leading end 22a of element 22. As stated above, the resistive load 40 is concentrated in the leading end portion of element 22. As a result, the distance L from leading end 22a of element 22 affects the length of the heat path between resistive load 40 to contact portion 60. Generally, the smaller the distance L, the higher the temperature of screen 30 for a particular temperature of element 22.

As a result, both the distance L and the contact area $S_3$ between screen 30 and element 22 can be optimized to achieve a desired temperature of screen 30 for a particular temperature of element 22. Furthermore, as stated above, the distance L also determines the relative location of contact portion 60 which should be adjusted such that contact portion 60 is not aligned with openings 44 in inner cover 26.

A further design consideration is the desire to maintain screen 30 at a sufficient temperature such that poisoning of screen 30 does not occur. For example, maintaining an adequate temperature of screen 30 can prevent the formation of silicone, carbon, sulfur and other components of the exhaust gas stream on screen 30 which could poison screen 30 and reduce the size of or plug openings 54.

Another design consideration is the spacing or gap 62 between screen 30 and element 22. The smaller the gap 62, the smaller the size and/or thermal mass of screen 30. A reduction in the size or thermal mass of screen 30 can result in less material being utilized and provide a lower cost and a reduced energy consumption, which also reduces cost. However, this must be balanced against the desire for a sufficient gap 62 such that when water droplets are present, the water droplets can hit screen 30 without also hitting element 22.

Another design consideration is the spacing or clearance provided by gap 50 between screen 30 and inner cover 26. If gap 50 is not present, screen 30 will contact inner cover 26 and a heat transfer path between screen 30 and inner cover 26 will result, increasing energy consumption as heat is transferred from screen 30 to inner cover 26. Thus, maintaining a gap 50 between screen 30 and inner cover 26 can reduce the energy consumption. If desired, a thermal insulator, or other separate component, or material can be provided between the base end flanges of inner cover 26 and screen 30 to provide thermal insulation therebetween.

Accordingly, a variety of different design considerations can come into play in selecting and designing the configuration for screen 30 and gas sensor 20. The interaction of these various design considerations may result in configurations of screen 30 and gas sensor 20 that can vary based on the desired performance, level of protection and/or the application in which gas sensor 20 is to be utilized.

As shown in FIGS. 1-3 and 7-9, screen 30 can be of a one-piece integral construction. The one-piece nature of screen 30 can reduce the cost and complexity of screen 30 and facilitate the manufacture of screen 30 and that of gas sensor 20. The direct heat-transferring contact between screen 30 and gas sensor 20 facilitates the heating of screen 30 by resistive load 40. The direct contact avoids the use of intermediate components being disposed between screen 30 and element 22 such that would reduce the efficiency therebetween. Additionally, the continuous contact between screen 30 and element 22 can provide a high reliability of gas sensor 20 as movement of screen 30 or a heat-conducting component relative to element 22 is not needed. Furthermore, this direct contact simplifies the construction by eliminating the need for intermediate members or movable components. The continuous contact between screen 30 and element 22 that circumscribes element 22 can provide a significant area $S_3$ of heat-transferring contact such that the efficiency of the heat transfer can be increased. The use of one or more covers 26, 28 can provide additional protection to gas sensor 20. It should be appreciated, however, that in some applications gas sensor 20 can be configured with only screen 30 surrounding leading end 22a of element 22 and the use of inner and outer covers 26, 28 avoided.

It should be appreciated that while the gas sensor 20 and screen 30 are shown in a configuration associated with a thimble type sensor, the present teachings are applicable to other types of sensors. For example, the present teachings can be utilized in planar type sensors, wherein the heating element and sensor may be a single element and may be more vulnerable to thermal stresses or shock and potential damage. Moreover, the sensors can be a switching type sensor, as shown herein, or a wide range or lambda type sensor. Additionally, the sensors can be operable to detect different types of gases within the exhaust gas flow. By way of non-limiting example, gas sensor 20 can be an $O_2$ sensor, an air/fuel sensor, and a NOx sensor. Moreover, sensors that have brittle elements that can be susceptible to thermal shocks or stresses as a result of contact with a liquid may benefit from the use of a heated protective screen according to the present teachings. Thus, the preceding description is exemplary in nature. Furthermore, it should be appreciated that while various configurations are shown and discussed, the various features utilized in these various configurations can be intermixed with one another to achieve a desired configuration and operational performance for gas sensor 20. As such, the configurations disclosed herein are not limited to those shown and the features can be combined, eliminated or altered from that shown.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A gas sensor comprising:
a gas-sensing element operative to detect a concentration of a specified gas in a gas flow;
a heating element operative to heat the gas-sensing element to an operating temperature;
a housing supporting the gas-sensing element;

a screen with a plurality of ventilation openings, the screen being disposed exterior to the gas-sensing element and surrounding the leading end portion of the gas-sensing element such that the gas flow travels through the ventilation openings prior to reaching the gas-sensing element, a first portion of the screen being in continuous direct heat-transferring contact with the gas-sensing element such that heat generated by the heating element is transferred to the screen through the gas-sensing element, and a second portion of the screen being spaced apart from the gas-sensing element with a first gap therebetween; and a band disposed on the screen and in continuous direct heat-transferring contact with the screen, the band circumscribing the first portion of the screen and being spaced apart from the gas-sensing element.

2. The gas sensor of claim 1, wherein the first portion of the screen is in continuous circumscribing direct contact with the gas-sensing element.

3. The gas sensor of claim 1, wherein the band includes a plurality of ventilation holes similar to the screen.

4. The gas sensor of claim 1, wherein the first portion includes at least one discrete area of continuous direct heat-transferring contact with the gas-sensing element.

5. The gas sensor of claim 1, wherein the screen is a single one-piece screen.

6. A gas sensor comprising:
a gas-sensing element operative to detect a concentration of a specified gas in a gas flow;
a heating element operative to heat the gas-sensing element to an operating temperature;
a housing supporting the gas-sensing element; and
a screen with a plurality of ventilation openings, the screen being disposed exterior to the gas-sensing element and surrounding a leading end portion of the gas-sensing element such that the gas flow travels through the ventilation openings prior to reaching the gas-sensing element, a first portion of the screen being in continuous direct heat-transferring contact with the gas-sensing element such that heat generated by the heating element is transferred to the screen through the gas-sensing element, and a second portion of the screen being spaced apart from the gas-sensing element with a first gap therebetween; wherein
the first portion includes at least one discrete area of continuous direct heat-transferring contact with the gas-sensing element;
the at least one discrete area of continuous direct heat-transferring contact is one of a plurality of discrete areas of continuous direct heat-transferring contact with the gas-sensing element.

7. The gas sensor of claim 6, wherein the plurality of discrete areas of continuous direct heat-transferring contact are arranged symmetrically around the gas-sensing element in a circumscribing manner.

8. A gas sensor comprising:
a gas-sensing element operative to detect a concentration of a specified gas in a gas flow;
a heating element operative to heat the gas-sensing element to an operating temperature;
a housing supporting the gas-sensing element;
a screen with a plurality of ventilation openings, the screen being disposed exterior to the gas-sensing element and surrounding a leading end portion of the gas-sensing element such that the gas flow travels through the ventilation openings prior to reaching the gas-sensing element, a first portion of the screen being in continuous direct heat-transferring contact with the gas-sensing element such that heat generated by the heating element is transferred to the screen through the gas-sensing element, and a second portion of the screen being spaced apart from the gas-sensing element with a first gap therebetween; and a first cover with at least one first opening, the first cover surrounding a leading end portion of the screen and the leading end portion of the gas-sensing element such that the gas flow travels through the at least one first opening prior to flowing through the ventilation openings and reaching the gas-sensing element, the first cover being spaced apart from the gas-sensing element with the screen disposed between the gas-sensing element and the first cover such that the first cover does not directly contact the gas-sensing element, a majority of the first cover being spaced apart from a majority of the screen such that a second gap exists between a majority of the first cover and screen, and the at least one first opening in the first cover is offset from the first portion of the screen.

9. The gas sensor of claim 8, further comprising a second cover with at least one second opening, the second cover surrounding the first cover, the screen, and the leading end portion of the gas-sensing element such that the gas flow travels through the at least one second opening prior to flowing through the at least one first opening, the ventilation openings, and reaching the gas-sensing element, a majority of the second cover being spaced apart from a majority of the first cover such that a third gap exists between the majority of the first and second covers.

10. The gas sensor of claim 9, wherein base end portions of the screen, the first cover, and the second cover are attached to a leading end of the housing.

11. The gas sensor of claim 8, wherein the ventilation openings are smaller than the at least one first opening.

12. A method of operating a gas sensor to detect a concentration of a specified gas in a gas flow while reducing a possibility of liquid droplets contacting the gas-sensing element, the method comprising:
surrounding a leading end portion of the gas-sensing element with a screen having a plurality of ventilation openings and disposed exterior to the gas-sensing element such that the gas flow travels through the ventilation openings prior to reaching the gas-sensing element, the screen having a first portion in continuous direct heat-transferring contact with the gas-sensing element and a second portion spaced apart from the gas-sensing element with a first gap therebetween;
heating the gas-sensing element to an operating temperature with a heating element;
heating the screen to an operating temperature with heat transfer from the gas-sensing element to the first portion of the screen;
evaporating liquid droplets in the gas flow that contact the screen; and
detecting the concentration of the specified gas in the gas flow.

13. The method of claim 12, further comprising providing a continuous circumscribing direct heat-transferring contact of the first portion with the gas-sensing element.

14. The method of claim 12, further comprising providing a band on the screen and in continuous direct heat-transferring contact therewith the band circumscribing the first portion of the screen and spaced apart from the gas-sensing element.

15. The method of claim 14, wherein providing the band includes providing a band with a plurality of ventilation openings similar to the screen.

16. The method of claim 12, further comprising providing a plurality of discrete areas of continuous direct heat-transferring contacts with the gas-sensing element with the first portion of the screen.

17. The method of claim 12, further comprising offsetting the at least one first opening from the first portion of the screen.

18. The method of claim 12, wherein surrounding the leading end portion of the gas-sensing element includes surrounding the leading end portion of the gas-sensing element with a single one-piece screen.

19. The method of claim 12, further comprising:
   surrounding the leading end portion of the gas-sensing element and a leading end of the screen with a first cover having at least one first opening such the gas flow travels through the at least one first opening prior to flowing through the ventilation openings and reaching the gas-sensing element, the first cover being spaced apart from the gas-sensing element with the screen therebetween such that the first cover does not directly contact the gas-sensing element; and
   surrounding the first cover, the screen and the leading end of the gas-sensing element with a second cover having at least one second opening such that the gas flow travels through the at least one second opening prior to flowing through the at least one first opening, the ventilation openings and reaching the gas-sensing element, and a majority portion of the second cover spaced apart from a majority portion of the first cover with a second gap therebetween.

* * * * *

UNITED STATES PATENT AND TRADEMARK OFFICE
CERTIFICATE OF CORRECTION

| | | |
|---|---|---|
| PATENT NO. | : 8,132,444 B2 | Page 1 of 1 |
| APPLICATION NO. | : 12/415468 | |
| DATED | : March 13, 2012 | |
| INVENTOR(S) | : Paul Cloutier et al. | |

It is certified that error appears in the above-identified patent and that said Letters Patent is hereby corrected as shown below:

Col. 4, line 9, "and" should be --an--

Col. 12, line 1, claim 19, after "such" insert --that--

Signed and Sealed this

Fourteenth Day of August, 2012

David J. Kappos
*Director of the United States Patent and Trademark Office*